United States Patent
Casey et al.

(10) Patent No.: US 10,590,364 B2
(45) Date of Patent: *Mar. 17, 2020

(54) QUATERNARY AMMONIUM SULFUR-CONTAINING BINUCLEAR MOLYBDATE SALTS AS LUBRICANT ADDITIVES

(71) Applicant: VANDERBILT CHEMICALS, LLC, Norwalk, CT (US)

(72) Inventors: Brian M. Casey, Norwalk, CT (US); Vincent J. Gatto, Milford, CT (US)

(73) Assignee: VANDERBILT CHEMICALS, LLC, Norwalk, CT (US)

( * ) Notice: Subject to any disclaimer, the term of this patent is extended or adjusted under 35 U.S.C. 154(b) by 89 days.

This patent is subject to a terminal disclaimer.

(21) Appl. No.: 16/045,327

(22) Filed: Jul. 25, 2018

(65) Prior Publication Data

US 2018/0327685 A1      Nov. 15, 2018

Related U.S. Application Data

(63) Continuation of application No. 15/432,410, filed on Feb. 14, 2017, now Pat. No. 10,059,901.

(60) Provisional application No. 62/298,743, filed on Feb. 23, 2016.

(51) Int. Cl.
| | |
|---|---|
| *C10M 135/18* | (2006.01) |
| *C10M 159/18* | (2006.01) |
| *C07C 211/63* | (2006.01) |
| *C10M 169/02* | (2006.01) |
| *C10M 125/22* | (2006.01) |
| *C10M 133/06* | (2006.01) |

(52) U.S. Cl.
CPC ......... *C10M 135/18* (2013.01); *C07C 211/63* (2013.01); *C10M 125/22* (2013.01); *C10M 133/06* (2013.01); *C10M 159/18* (2013.01); *C10M 169/02* (2013.01); *C10M 2201/066* (2013.01); *C10M 2207/1256* (2013.01); *C10M 2215/04* (2013.01); *C10M 2219/068* (2013.01); *C10M 2223/045* (2013.01); *C10M 2227/09* (2013.01); *C10N 2210/01* (2013.01); *C10N 2210/06* (2013.01); *C10N 2230/06* (2013.01); *C10N 2250/10* (2013.01)

(58) Field of Classification Search
CPC .............. C10M 125/22; C10M 135/18; C10M 2215/04; C10M 2219/068; C10M 2223/045; C10M 133/06; C10M 159/18; C10M 169/02; C10M 2201/066; C10M 2207/1256; C10M 2227/09; C10N 2230/06; C10N 2250/10; C10N 2210/01; C10N 2210/06; C07C 211/63
See application file for complete search history.

(56) References Cited

U.S. PATENT DOCUMENTS 3,356,702 A     12/1967 Farmer et al.
4,370,245 A *   1/1983 Ryu .................. C07F 11/005
                                          508/362
10,059,901 B2 * 8/2018 Casey ................ C10M 135/18
2004/0019043 A1 1/2004 Coucouvanis et al.
2005/0003970 A1 1/2005 Ohmura et al.
2014/0171348 A1 6/2014 Patil et al.
2017/0240838 A1 8/2017 Casey et al.

FOREIGN PATENT DOCUMENTS

| CA | 2831596 A1 | 10/2012 |
| WO | 8002836 A | 12/1980 |
| WO | 2015174987 A1 | 11/2015 |
| WO | 2017146939 A1 | 8/2017 |

OTHER PUBLICATIONS

D. Coucouvanis, A. Toupadakis, A. Hadjikyriacou, "Synthesis of thiomolybdenyl complexes with [Mo2(S)2(O)2]2+ cores and substitutionally labile ligands. Crystal and molecular structure of the tris(dimethylformamide)dioxotetrasulfidodimolybdenum complex", Inorg. Chem, 1988, 27, 3272-32 (Year: 1988).*
D. Coucouvanis et al., "Studies of the Reactivity of Binary Thio- and Tertiary Oxothiomolybdates toward Electrophiles. Reactions with Dicarbomethoxyacetylene and the Synthesis and Structures of the [Et4N]2[MoO(L)2], anti-[Et4N]2 [Mo2O2S2(L)2], syn-[Ph4P]2[Mo2O2S2(L)2]2DMF, [Ph4P]2[Mo(L)3] DMF C6H6, and [Ph4P]2[Mo2S2(L)4] 2CH2Cl2 Complexes (L=1,2-Dicarbomethoxy-1,2-ethylenedithiolate)"; Inorg. Chem. 1991, vol. 30, pp. 754-767.
R. S. Bikshandarkoil, "Does an all-sulphur analogue of heptomolybdate exit?", J. Chem. Sci. vol. 116, No. 5, Sep. 2004, pp. 251-259.
International Search Report for corresponding application PCT/US17/17800 dated Apr. 28, 2017.
D. Coucouvanis et al., "Synthesis of Thiomolybdenyl Compleses with Mo2(S)2(O)2]2+ Cores and Substitutionally Labile Ligands. Crystal and Molecular Structure of the [Mo2O2S4(DMF)3] Complex", (Inorg. Chem. 1988, vol. 27, pp. 3272-3273).

(Continued)

*Primary Examiner* — James C Goloboy
(74) *Attorney, Agent, or Firm* — Norris McLaughlin, P.A.

(57) ABSTRACT

The present invention relates to lubricating compositions comprising a compound of Formula I:

[Formula I]

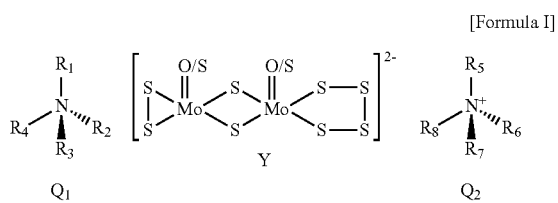

wherein $R_1$-$R_4$ and $R_5$-$R_8$ are independently selected from the group consisting of hydrocarbyl groups and hydrocarbyl groups containing heteroatoms, such that the total carbon atoms from counterions $Q_1$ and $Q_2$ is from 8 to 76, and molybdate anion (Y) is a binuclear sulfur-containing dianion selected from the group consisting of $[Mo_2S_8O_2]^{2-}$, $[Mo_2S_9O]^{2-}$, $[Mo_2S_{10}]^{2-}$, and mixtures thereof, and are present in the lubricating composition in an amount sufficient to provide about 100-15,000 ppm molybdenum.

25 Claims, No Drawings

(56) References Cited

OTHER PUBLICATIONS

D. Coucouvanis et al. and Recatalá et al., "Reaction of MoO42- and WO42—with Aqueous Polysulfides: Synthesis, Structure, and Electrochemistry of η-Polysulfido Complexes Containing a Bridging S,S {M2O2S2}2+ (M=Mo, W) Core" (Dalton Trans., 2013, 42, 12947-12955).
D. Coucouvanis, A. Toupadakis, A. Hadjikyriacou, "Synthesis of thiomolybdenyl complexes with [Mo2(S)2(0)2]2+ cores and substitutionally labile ligands. Crystal and molecular structure of the tris(dimethylformamide) dioxotetrasulfidodimolybdenum complex", Inorg. Chem, 1988, 27, 3272-3273.
Clegg, W., Christou, G., Garner, C.D., Sheldrick, G.M., "[Mo2S10]2-, a complex with Terminal Sulfide, Bridging Sulfido, Persulfido, and Tetrasulfido Groups", Inorg. Chem., 1981, 20, 1562-1566.
Written Opinion of the International Searching Authority for corresponding application PCT/US17/17800 dated Apr. 28, 2017.
International Preliminary Report on Patentability for corresponding application PCT/US2017/017800 dated Aug. 28, 2018.

\* cited by examiner

QUATERNARY AMMONIUM SULFUR-CONTAINING BINUCLEAR MOLYBDATE SALTS AS LUBRICANT ADDITIVES

This application is a continuation of U.S. application Ser. No. 15/432,410, filed Feb. 14, 2017, which claims priority benefit of U.S. Provisional Application No. 62/298,743, filed Feb. 23, 2016, the disclosures of each of which patent applications are incorporated herein by reference.

FIELD OF THE INVENTION

This invention concerns compounds useful as an additive in lubricants and greases for friction reduction, wear reduction, and/or extreme pressure performance.

Described herein is the development of highly sulfurized binuclear molybdate salts with application as additives in lubricants. This class of compounds may be represented by the following formula:

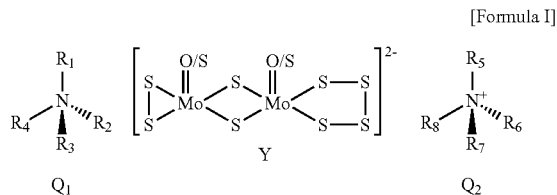

[Formula I]

where a molybdenum salt is prepared which comprises two countercations ($Q_1$ and $Q_2$) and a binuclear sulfur-containing molybdate anion (Y).

Discussion of and Comparison with Related Art

This invention involves the application of the class of compounds first described in Coucouvanis et al. (*Inorg. Chem.* 1988, 27, 3272-3273) as additives in lubricants for friction reduction, wear reduction, and extreme pressure performance. Coucouvanis et al. teach synthesis of thiomolybdenyl complexes with $[Mo_2S_2O_2]^{2+}$ cores and substitutionally labile ligands. Bhattacharyya et al. demonstrate the preparation of ($Me_4N$)- and ($Et_4N$)-based compounds and provide additional confirmation of the $[Mo_2S_2O_2]^{2+}$ core with x-ray crystallography (*Inorg. Chem.* 1991, 30, 3948-3955). The inventors of this application have broadened the scope of the countercations described previously, resulting in compounds with lower melting points. In some cases, room-temperature ionic liquids are obtained.

According to U.S. Pat. No. 4,370,245, certain tetrahydrocarbylammonium thiomolybdates containing at least about 15 carbon atoms, such as trioctylmethylammonium thiomolybdate, enhances the extreme pressure properties of substituted-thickened urea greases. The compound used in the invention described herein differs from the compound of the '245 patent in that the core of the sulfur-containing molybdate structure is distinct from thiomolybdate $(MoS_4)^{2-}$. The molybdenum core of the class of compounds described herein is binuclear with respect to molybdenum and is composed of oxygen and/or sulfur.

U.S. Pat. No. 3,356,702 describes a class of dithiocarbamates having the general formula $MoO_2(SCSNR_2)_2$. The compound used in the invention described herein differs from the compound of the '702 patent in that the compounds described herein are molybdenum-containing salts rather than neutral organometallic compounds. In addition, the molybdenum-containing salt has a higher sulfur to molybdenum ratio than the molybdenum dithiocarbamate technology.

This class of additives improves upon current technology such as molybdenum dithiocarbamates and molybdenum disulfide by increasing the sulfur to molybdenum ratio. These high-sulfur containing additives exhibit good performance in terms of friction reduction, wear reduction, and/or extreme pressure properties. Furthermore, selection of appropriate quaternary ammonium countercations can result in products that are low-melting solids or room-temperature ionic liquids.

The preparation methods of the molybdenum-containing salts described in Coucouvanis et al. and Recatalá et al. (*Dalton Trans.*, 2013, 42, 12947-12955) were modified by the inventors of this application to improve removal of unreacted elemental sulfur. The preparation methods described herein remove excess sulfur from the reaction mixture with an appropriate solvent (i.e. acetonitrile or carbon disulfide) and avoid a recrystallization step. The extraction solvent and unreacted sulfur can be separated by distillation and recycled in the process.

SUMMARY OF THE INVENTION

The present invention relates to lubricating compositions comprising a compound of Formula I:

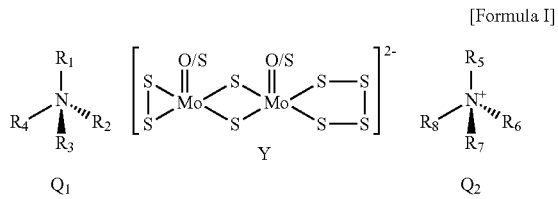

[Formula I]

wherein $R_1$-$R_4$ and $R_5$-$R_8$ are independently selected from the group consisting of hydrocarbyl groups and hydrocarbyl groups containing heteroatoms, such that the total carbon atoms from counterions $Q_1$ and $Q_2$ is from 8 to 76, and molybdate anion (Y) is a binuclear sulfur-containing dianion selected from the group consisting of $[Mo_2S_8O_2]^{2-}$, $[Mo_2S_9O]^{2-}$, $[Mo_2S_{10}]^{2-}$, preferably $[Mo_2S_8O_2]^{2-}$, wherein the total molybdenum content of the compound of Formula I ranges from about 10% to about 31%, and mixtures thereof. Lubricants containing the compound of Formula I as a single component or in combination with other additives have demonstrated improved performance with respect to friction reduction, wear reduction, and/or extreme pressure properties. The present invention further relates to the compound of Formula I as defined above, wherein the total carbon atoms from counterions $Q_1$ and $Q_2$ is from 12 to 76 and the total molybdenum content of the compound of Formula I ranges from 10% to 28%.

DETAILED DESCRIPTION OF THE INVENTION

Lubricants typically require multiple additives in order to improve the overall performance. The class of compounds described in this application, when used as a single component additive or in combination with other lubricant additives, imparts improved friction reduction, wear reduction, and/or extreme pressure performance over the base lubricant. One advantage of this new quaternary ammonium sulfur-containing molybdate technology is that it allows the use of fewer total additives for imparting extreme pressure and antiwear improvements. Another benefit is that it can deliver high levels of both molybdenum and sulfur for boosting extreme pressure and antiwear performance.

Highly Sulfurized Binuclear Molybdate Salts

Described herein is the development of highly sulfurized binuclear molybdate salts with applications as additives in lubricants. Lubricants containing these additives as a single component or in combination with other additives have demonstrated improved performance with respect to friction reduction, wear reduction, and/or extreme pressure properties. This class of compounds may be represented by the following formula:

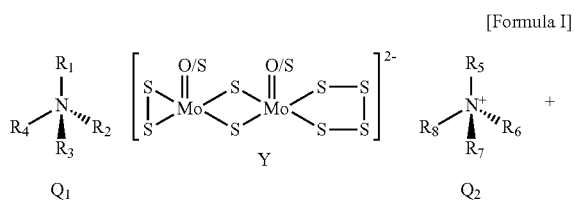

[Formula I]

where a molybdenum salt is prepared which comprises two countercations ($Q_1$ and $Q_2$) and a binuclear sulfur-containing molybdate anion (Y). For the countercations, $Q_1$ and $Q_2$ are quaternary ammonium ions comprising groups $R_1$-$R_4$ and $R_5$-$R_8$ that are independently selected from hydrocarbyl groups and/or hydrocarbyl groups containing heteroatoms (e.g. oxygen, nitrogen, and sulfur) such that the total carbon atoms from $Q_1$ and $Q_2$ is 8-76 carbon atoms, preferably 8-32, carbon atoms. The hydrocarbyl groups can be straight-chain, branched, or cyclic hydrocarbons and saturated or unsaturated hydrocarbons from 0 to 18, from 1 to 18 or preferably 2-16 or 1-4 carbon atoms each. The quaternary ammonium countercations can be the same ($Q_1=Q_2$), different ($Q_1 \neq Q_2$), or a mixture of two different countercations of variable ratio (ranging from $Q_1:Q_2$=100:0 to 0:100). Additionally, $R_{1-3}$ and $R_{5-2}$ can be as defined above and $R_4$ and $R_8$ may be taken together as a mono- or polyalkylene (e.g. ethylene or propylene) oxide such that $Q_1$ and $Q_2$ are linked. Molybdate anion (Y) is a binuclear sulfur-containing dianion composed of $[Mo_2S_8O_2]^{2-}$, $[Mo_2S_9O]^{2-}$, $[Mo_2S_{10}]^{2-}$, or mixtures thereof.

Also described herein is a compound of Formula I as defined above, wherein the total carbon atoms from counterions $Q_1$ and $Q_2$ is from 12 to 76 and the total molybdenum content of the compound of Formula I ranges from 10% to 28%.

In particular embodiments, the highly sulfurized binuclear molybdate salts include compounds where $Q_1=Q_2$=tetramethylammonium ($Me_4N$), tetraethylammonium ($Et_4N$), tetra-n-butylammonium ($nBu_4N$), tetra-n-octylammonium ($nOct_4N$), methyltri-n-octylammonium ($MenOct_3N$), hexadecyltrimethylammonium ($CetylMe_3N$), and di(dehydrogenated tallowalkyl)dimethylammonium ($DitallowMe_2N$), and $Y=[Mo_2S_8O_2]^{2-}$, which can be used as lubricant additives at treat rates in the range of 0.1-10.000 wt. %, preferably 0.5-5.00 wt. %, more preferably 1-4.00 wt. %, and yet more preferably 2-4.00 wt. % or 3-4.00 wt. %. In a particularly preferred embodiment, the highly sulfurized binuclear molybdate salt can be bis(tetramethylammonium) oxothiomolybdate salt $(Me_4N)_2[Mo_2S_8O_2]$ and/or bis(tetraethylammonium) oxothiomolybdate salt, $(Et_4N)_2[Mo_2S_8O_2]$ or bis(tetrabutylammonium) oxothiomolybdate salt $(Bu_4N)_2$ $[Mo_2S_8O_2]$. Bis(tetramethylammonium) oxothiomolybdate salt $(Me_4N)_2[Mo_2S_8O_2]$ is preferred because as an additive it can deliver very high levels of molybdenum and sulfur to a lubricating oil composition. Bis(tetrabutylammonium) oxothiomolybdate salt $(Bu_4N)_2[Mo_2S_8O_2]$ is preferred because it exists as a room temperature ionic liquid. In an embodiment, molybdenum-containing additives are useful at treat rates sufficient to deliver 100-15,000 ppm, preferably 1000-10,000 ppm, more preferably 2,800-14,000 ppm, and yet more preferably 2,800-8,400 ppm of molybdenum to the finished product.

This class of compounds is the product from the reaction of ammonium heptamolybdate tetrahydrate, sulfur, and a quaternary ammonium salt consisting of a quaternary ammonium countercation ($Q_1$ and/or $Q_2$) and an anion. The anion is selected such that the byproduct ammonium salt generated at the end of the reaction is aqueous soluble. Examples of anions include but are not limited to halides (fluoride, chloride, bromide, and/or iodide), hydroxide, borates, sulfate, alkylsulfates, bisulfite, sulfite, bicarbonate, carbonates, chlorate, bromate, and/or carboxylates (e.g. acetate). Depending on the identities of $Q_1$ and $Q_2$, the product quaternary ammonium sulfur-containing molybdate salt can be a powder, a low-melting solid (melting point at temperatures ≤50° C.), or a room-temperature ionic liquid. Representative examples for the preparation of the class of compounds of the instant invention are provided in Example 1.

Individual compounds from this class of molecules can be used as additives in lubricants and greases for friction reduction, wear reduction, and/or extreme pressure performance at a treat rate from 0.1-10.000 wt. %, preferably 0.5-5.00 wt. %, more preferably 1-4.00 wt. %, and yet more preferably 2-4.00 wt. % or 3-4.00 wt. %. In an embodiment, molybdenum-containing additives are useful at treat rates sufficient to deliver 100-15,000 ppm, preferably 1000-10,000 ppm, more preferably 2,800-14,000 ppm, and yet more preferably 2,800-8400 ppm of molybdenum to the finished product. Furthermore, these compounds can be used in combination with other additives such as dispersants, detergents, viscosity modifiers, antioxidants, friction modifiers, antiwear agents, corrosion inhibitors, rust inhibitors, salts of fatty acids (soaps), and extreme pressure additives.

A preferred application is the use of quaternary ammonium binuclear oxothiomolybdates in a lubricant or grease in combination with a zinc-based or phosphorus-based antiwear additive. Examples of zinc-based antiwear additives include zinc dialkyldithiocarbamate (VANLUBE® AZ, VANLUBE® ZDC) and zinc carboxylate (VANLUBE® LVZ). Examples of phosphorus-based antiwear additives include triphenyl phosphate, triphenyl thiophosphate (IRGALUBE® TPPT), trialkylphenyl thiophosphate (IRGALUBE® 211, IRGALUBE® 232), 1,2-dicarbobutoxyethyl-o,o-dialkylphosphorodithioate dialkyl fumarate (VANLUBE® 7611 M, VANLUBE® 727), amine salts of alkyl acid phosphates (VANLUBE® 672, VANLUBE® 672 E, VANLUBE® 692, VANLUBE® 692 E, VANLUBE® 9123, IRGALUBE® 349) alkyl-3-[[bis(1-methylethoxy)phosphinothioyl]thio]propionate (IRGALUBE® 63), antimony o,o-dialkylphosphorodithioate (VANLUBE® 622), and dialkylphosphite (IRGALUBE® OPH). An example of a zinc and phosphorus-based anti-wear additive is zinc dialkyldithiophosphate (ZDDP or ZDTP). It may be necessary, in certain applications, to use these quaternary ammonium binuclear oxothiomolybdates in combination with corrosion or rust inhibitors. Examples of corrosion and rust inhibitors that may be used include liquid imidazoline derivatives (VANLUBE® RI-G, AMINE O), liquid alkenyl succinic acid derivatives (VANLUBE® RI-A, IRGACOR® L 12), N-oleyl sarcosine (SARKOSYL® 0), benzotriazole, tolutriazole, liquid tolutriazole derivatives (IRGAMET® 39, CUVAN® 303), liquid triazole derivatives (IRGAMET® 30), alkylated diphenylamine derivatives of tolutriazole (VANLUBE® 887, VANLUBE® 887 E), 2,5-dimercapto-1,3,4-thiadiazole derivatives (CUVAN® 484, CUVAN® 826), 5,5-dithiobis(1,3,4-thiadiazole-2(3H)-thione) (VANLUBE® 829), and salts of dinonylnaphthalene sulfonates (VANLUBE® RI-BSN, VANLUBE® RI-CSN, VANLUBE® RI-ZSN). There may be situations where an improvement in oxidative stability of the grease or lubricant is required. In such a situation supplemental antioxidants would be used.

Examples of antioxidants include alkylated diphenylamines (VANLUBE® 81, VANLUBE® 961, VANLUBE® SS, VANLUBE® NA, IRGANOX® L 57, IRGANOX® L 67, NAUGALUBE® 438 L, NAUGALUBE® 640), hindered phenolic antioxidants (ETHANOX® 4701, ETHANOX® 4702, ETHANOX® 4703, ETHANOX® 4716 IRGANOX® L 135, IRGANOX® L 101, IRGANOX® L 107, IRGANOX® L 109, IRGANOX® L 115, VANLUBE® BHC), butylated hydroxytoluene (BHT), phenyl-α-naphthylamine (PANA), alkylated phenyl-α-naphthylamine (VANLUBE® 1202, IRGANOX® L 06, NAUGALUBE® APAN), derivatives of alkylated phenyl-α-naphthylamine (VANLUBE® 9317), and polymerized 1,2-dihydro-2,2,4-trimethylquinoline (VANLUBE® RD). Additives containing other elements such as tungsten, boron, copper, titanium, calcium, magnesium, lithium, barium may also be used. Two very useful additives for reducing friction and wear that may be used are sold commercially as VANLUBE® W-324, an organotungsten-based additive, and VANLUBE® 289, an organoboron-based additive.

Additional sulfur chemistry should not be required when formulating a grease or lubricant with these quaternary ammonium binuclear oxothiomolybdates as they inherently have such a high level of sulfur. However, if supplemental sulfur is needed it can be added through the use of sulfurized olefins (VANLUBE® SB), sulfurized fats and oils, ashless dithiocarbamates (VANLUBE® 7723, VANLUBE® 981), or 2,5-dimercapto-1,3,4-thiadiazole derivatives (VANLUBE® 871).

Additional molybdenum chemistry should not be required when formulating a grease or lubricant with these quaternary ammonium binuclear oxothiomolybdates as they inherently have such a high level of molybdenum. However, if supplemental molybdenum is needed it can be added through the use of molybdenum dithiocarbamates (MOLYVAN® A, MOLYVAN® 807, MOLYVAN® 822, MOLYVAN® 3000), molybdenum thiophosphates (MOLYVAN® L), or molybdenum ester/amide complexes (MOLYVAN® 855). The combination of these quaternary ammonium binuclear oxothiomolybdates and molybdenum dithiocarbamates is particularly preferred.

Treat levels for all the above mentioned additives known in the art, which can be used in combination with the highly sulfurized binuclear molybdate salts described herein, can vary significantly depending upon the application, additive solubility, base fluid type, and finished fluid performance requirements. Typical treat levels usually vary from 0.005 wt. % to 10.000 wt. %, preferably 0.01-10.000 wt. %, 0.1-10.000 wt. %, or 1-10.000 wt. %, based on the type of finished lubricant being developed.

In embodiments of the present invention, the treat rates for all additives used in combination with molybdenum do not exceed 1.00 wt. %, preferably the treat rates do not exceed 0.5 wt. %.

Base Oils

The base oils employed as lubricant vehicles are typically oils used in automotive and industrial applications such as, among others, turbine oils, hydraulic oils, gear oils, crankcase oils and diesel oils. The base stock may comprise at least 90%, or at least 95% by weight of the total lubricant composition.

Typical lubricant basestocks that can be used in this invention may include natural base oils, including mineral oils, petroleum oils, paraffinic oils and vegetable oils, as well as oils derived from synthetic sources.

In particular, lubricant basestocks that can be used in this invention may be petroleum-based or synthetic stocks including any fluid that falls into the API basestock classification as Group I, Group II, Group III, Group IV, and Group V. The hydrocarbon base oil may be selected from naphthenic, aromatic, and paraffinic mineral oils.

Suitable synthetic oils may also be selected from, among others, ester-type oils (such as silicate esters, pentaerythritol esters and carboxylic acid esters), esters, diesters, polyol esters, polyalphaolefins (also known as PAOS or poly-α-olefins), hydrogenated mineral oils, silicones, silanes, polysiloxanes, alkylene polymers, polyglycol ethers, polyols, bio-based lubricants and/or mixtures thereof.

Grease

Base grease compositions consist of lubricating oil and a thickener system. Generally, the base oil and thickener system will comprise 65 to 95, and 3 to 10 mass percent of the final grease respectively. The base oils most commonly used are petroleum oils, bio-based oils or synthetic base oils. The most common thickener system known in the art are lithium soaps, and lithium-complex soaps, which are produced by the neutralization of fatty carboxylic acids or the saponification of fatty carboxylic acid esters with lithium hydroxide typically directly in the base fluids. Lithium-complex greases differ from simple lithium greases by incorporation of a complexing agent, which usually consists of di-carboxylic acids.

Other thickener systems that can be used include aluminum, aluminum complex, sodium, calcium, calcium complex, organo-clay, sulfonate and polyurea, etc.

Other Additives

The compounds of the instant invention can be used in combination with additional additives including but not limited to dispersants, detergents, viscosity modifiers, antioxidants, friction modifiers, antiwear agents, corrosion inhibitors, rust inhibitors, salts of fatty acids (soaps), and extreme pressure additives.

Throughout this application, various publications are referred to. Disclosures of these publications in their entireties are hereby incorporated by reference into this application in order to more fully describe the state of the art as of the date of the invention described herein.

It is understood that where a parameter range is provided, all integers within that range, and tenths thereof, are also provided by the invention.

For the embodiments described in this application, each embodiment disclosed herein is contemplated as being applicable to each of the other disclosed embodiments.

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

Example 1: Preparation of Compounds of the Instant Invention

The following procedure is a representative example for the preparation of the class of compounds of the instant invention: 7.42 g of ammonium heptamolybdate tetrahydrate is dissolved in 300 mL of water in a 4-neck flask with a mechanical stirrer. Then, 11.16 g of sulfur is dissolved in 52.81 g of a 20% aqueous solution of ammonium sulfide and slowly added to the reaction. The reaction is stirred for 16 hours. A solution of 8.83 g of tetraethylammonium bromide in 125 mL of water is prepared and added dropwise to the reaction mixture via an addition funnel. The reaction is stirred for an additional 2 hours at room temperature. The precipitate is filtered and the solids are washed with water until the filtrate is colorless. The solids are suspended in 300 mL of acetonitrile and stirred for an additional 30 minutes. The mixture is filtered and the solids are washed with acetonitrile. The acetonitrile is removed from the filtrate by distillation on a rotary evaporator to yield the product as a deep red-orange powder that contains 24.4 wt. % Mo and 36.7 wt. % S.

In carrying out the above reaction, a variety of quaternary ammonium salts may be used. For example, when tetraethylammonium is employed, the counteranion may be fluoride, chloride, bromide, iodide, hydroxide, borate, carbonate, bicarbonate, bisulfite, sulfite, bisulfonate, sulfate, alkylsulfates, chlorate, bromate, and carboxylate (e.g. acetate). Additional tetraalkylammonium countercations that may be used include, but are not limited to, tetramethylammonium, alkyltrimethylammonium (e.g. ethyl-, butyl-, hexyl-, octyl-, decyl-, dodecyl-, tetradecyl-, hexadecyl- and octadecyltrimethylammonium), dialkyldimethylammonium (e.g. diethyl-, dibutyl-, dihexyl-, dioctyl-, didecyl-, didodecyl-, ditetradecyl-, dihexadecyl-, and dioctadecyldimethylammonium), trialkylmethyl-ammonium (e.g. triethyl-, tributyl-, trihexyl-, trioctyl-, tridecyl-, tridodecyl-, tritetradecyl-, trihexadecyl-, and trioctadecyl methylammonium), alkylbenzyldimethylammonium (e.g. ethyl-, butyl-, hexyl-, octyl-, decyl-, dodecyl-, tetradecyl-, hexadecyl-, and octadecylbenzyldimethylammonium), tetrabutylammonium, tetrahexylammonium, tetraoctylammonium, tetradecylammonium, tetradodecylammonium, tetratetradecylammonium, tetrahexadecylammonium, and tetraoctadecylammonium. In addition, the quaternary ammonium cation may include, as part of the various alkyl chains, oxygen-containing functional groups. For example, ethoxylated and propoxylated ammonium salts may be employed. Quaternary ammonium salts containing ether or ester linkages may be employed as well. Examples of such ammonium salts include, but are not limited to, alkanoylcholines (e.g. acetyl-, octanoyl-, decanoyl-, dodecanoyl-, tetradecanoyl-, hexadecanoyl-, and octadecanoyl-choline), N,N-bis(hydroxyethyl)-N,N-dialkylammonium (e.g. N,N-bis(hydroxyethyl)-N-tallow-N-ethyl-ammonium, N,N-bis(hydroxy-ethyl)-N-coco-N-methylammonium, and N,N-bis(hydroxy-ethyl)-N,N-diethyl-ammonium), N,N-diethoxylated-N,N-dialkylammonium (e.g. N,N-diethoxylated-N-tallow-N-ethylammonium, N,N-diethoxylated-N-coco-N-methylammonium, and N,N-diethoxylated-diethyl-ammonium), N,N-dipropoxylated-N,N-dialkylammonium (e.g. N,N-dipropoxylated-N-tallow-N-ethylammonium, N,N-dipropoxylated-N-coco-N-methylammonium, and N,N-dipropoxylated-diethylammonium), N,N-dialkyl-N,N-bis[2-(alkoxycarbonyl) ethyl]-ammonium (e.g. N,N-dimethyl-N,N-bis[2-(alkoxycarbonyl)ethyl] ammonium), and N,N,N-tris[2-(alkanoyloxy)ethyl]-N-alkyl-ammonium (e.g. N,N,N-tris[2-(acetyloxy)ethyl]-N-methylammonium, N,N,N-tris[2-(cocoyloxy)-ethyl]-N-methylammonium), and N,N,N-tris[2-(tallowoyl-oxy)ethyl]-N-methylammonium). The quaternary ammonium cations may also be taken together forming a dication using a mono- or polyalkylene (e.g. ethylene or propylene) oxide linker. Examples of such include but are not limited to (oxydiethylene)bis(trimethylammonium) and (oxydipropylene)bis(trimethyl-ammonium).

The following examples of this class of compounds were prepared where $Q_1=Q_2$ and $Y=[Mo_2S_8O_2]^{2-}$: tetramethylammonium ($Me_4N$), tetraethylammonium ($Et_4N$), tetra-n-butylammonium ($nBu_4N$), tetra-n-octylammonium ($nOct_4N$), methyltri-n-octylammonium ($MenOct_3N$), hexadecyltrimethylammonium ($CetylMe_3N$), and di(dehydrogenated tallowalkyl)dimethylammonium ($DitallowMe_2N$). In addition, a sample was prepared where $Q_1 \neq Q_2$ ($Q_1=Me_4N$, $Q_2=Et_4N$) and $Y=[Mo_2S_8O_2]^{2-}$. Table 1 lists the physical properties of a variety of quaternary ammonium binuclear oxothiomolybdate salts that were prepared:

TABLE 1

| Quaternary ammonium oxothiomolybdate | Mo (wt. %) | S (wt. %) | N (wt. %) | C (wt. %) | H (wt. %) | mp (° C.)[1] |
|---|---|---|---|---|---|---|
| $(Me_4N)_2[Mo_2S_8O_2]$ | 30.6 | 41.7 | 4.7 | 15.3 | 3.7 | 207.3, 240.3, 267.4 (decomp.) |
| $(Et_4N)_2[Mo_2S_8O_2]$ | 24.4 | 36.7 | 3.9 | 26.8 | 6.2 | 160, 200.0 (decomp.) |
| $(Me_4N)(Et_4N)[Mo_2S_8O_2]$ | 27.9 | 38.2 | 4.2 | 21.7 | 4.8 | 164.7 |
| $(nBu_4N)_2[Mo_2S_8O_2]$ | 18.9 | 25.4 | 3.2 | 38.9 | 8.1 | RTIL |
| $(nOct_4N)_2[Mo_2S_8O_2]$ | 12.2 | 17.4 | 2.7 | 54.6 | 10.3 | RTIL |
| $(CetylMe_3N)_2[Mo_2S_8O_2]$ | 17.5 | 25.3 | 2.8 | 44.3 | 8.4 | 85.8, 208.2 (decomp.) |
| $(DitallowMe_2N)_2[Mo_2S_8O_2]$ | 9.6 | 17.3 | 2.2 | 57.6 | 10.7 | 40.9, 156.6 (decomp.) |
| $(MenOct_3N)_2[Mo_2S_8O_2]$ | 13.2 | 22.1 | 2.5 | 9.7 | 51 | RTIL |
| Molybdenum Dithiocarbamate | Mo (wt. %) | S (wt. %) | N (wt. %) | C (wt. %) | H (wt. %) | mp (° C.) |
| MOLYVAN ® A | 27.0-29.0 | 23.5-25.5 | — | — | — | 258 |

[1]RTIL—Room-temperature ionic liquid

Example 1.1 Preparation of Exemplary Compounds

Preparation of $(Me_4N)_2[Mo_2S_8O_2]$ 14.84 g of ammonium heptamolybdate tetrahydrate is dissolved in 400 mL of water in a 4-neck flask with a mechanical stirrer. Then, 22.32 g of sulfur is dissolved in 105.60 g of a 20% aqueous solution of ammonium sulfide and slowly added to the reaction. The reaction is stirred for 16 hours. A solution of 9.21 g of tetramethylammonium chloride in 200 mL of water is prepared and added dropwise to the reaction mixture via an addition funnel. The reaction is stirred for an additional 1.5 hours at room temperature. The precipitate is filtered and the solids are washed successively with ethanol (three times with 100 mL), carbon disulfide (three times with 100 mL), and petroleum ether (three times with 100 mL). The remaining solid is dried under a stream of air for 1 hr to give a light orange-brown powder that contains 30.6 wt. % Mo and 41.7 wt. % S.

Example 1.2 Preparation of Exemplary Compounds

Preparation of $(Et_4N)_2[Mo_2S_8O_2]$ 7.42 g of ammonium heptamolybdate tetrahydrate is dissolved in 300 mL of water in a 4-neck flask with a mechanical stirrer. Then, 11.16 g of sulfur is dissolved in 52.81 g of a 20% aqueous solution of ammonium sulfide and slowly added to the reaction. The reaction is stirred for 16 hours. A solution of 8.83 g of tetraethylammonium bromide in 125 mL of water is prepared and added dropwise to the reaction mixture via an addition funnel. The reaction is stirred for an additional 2 hours at room temperature. The precipitate is filtered and the solids are washed with water until the filtrate is colorless. The solids are suspended in 300 mL of acetonitrile and stirred for an additional 30 minutes. The mixture is filtered and the solids are washed with acetonitrile. The acetonitrile is removed from the filtrate by distillation on a rotary evaporator to yield the product as a deep red-orange powder that contains 24.4 wt. % Mo and 36.7 wt. % S.

Alternative Preparation of $(Et_4N)_2[Mo_2S_8O_2]$ 14.84 g of ammonium heptamolybdate tetrahydrate is dissolved in 400 mL of water in a 4-neck flask with a mechanical stirrer. Then, 22.32 g of sulfur is dissolved in 105.60 g of a 20% aqueous solution of ammonium sulfide and slowly added to the reaction. The reaction is stirred for 16 hours. A solution of 17.65 g of tetraethylammonium bromide in 200 mL of water is prepared and added dropwise to the reaction mixture via an addition funnel. The reaction is stirred for an additional 1.5 hours at room temperature. The precipitate is filtered and the solids are washed successively with ethanol (three times with 100 mL), carbon disulfide (three times with 100 mL), and petroleum ether (three times with 100 mL). The remaining solid is dried under a stream of air for 1 hr to give an orange-brown powder that contains 24.8 wt. % Mo and 36.2 wt. % S.

Example 1.3 Preparation of Exemplary Compounds

Preparation of $(Me_4N)(Et_4N)[Mo_2S_8O_2]$ 14.84 g of ammonium heptamolybdate tetrahydrate is dissolved in 400 mL of water in a 4-neck flask with a mechanical stirrer. Then, 22.32 g of sulfur is dissolved in 105.60 g of a 20% aqueous solution of ammonium sulfide and slowly added to the reaction. The reaction is stirred for 16 hours. A mixture of 8.83 g of tetraethylammonium bromide and 4.60 g tetramethylammonium chloride is dissolved in 200 mL of water and added dropwise to the reaction mixture via an addition funnel. The reaction is stirred for an additional 1.5 hours at room temperature. The precipitate is filtered and the solids are washed successively with ethanol (three times with 100 mL), carbon disulfide (three times with 100 mL), and petroleum ether (three times with 100 mL). The remaining solid is dried under a stream of air for 1 hr to give an orange-brown powder that contains 27.9 wt. % Mo and 38.2 wt. % S.

Example 1.4 Preparation of Exemplary Compounds

Preparation of $(nBu_4N)_2[Mo_2S_8O_2]$ 2.47 g of ammonium heptamolybdate tetrahydrate is dissolved in 100 mL of water in a round bottom flask with a magnetic stirrer. Then, 3.72 g of sulfur is dissolved in 17.70 g of a 20% aqueous solution of ammonium sulfide and slowly added to the reaction. The reaction is stirred for 24 hours. A solution of 3.97 g of tetra-n-butylammonium bromide in 42 mL of water is prepared and added dropwise to the reaction mixture via an addition funnel. The reaction is stirred for an additional 2 hours at room temperature. The upper aqueous layer is decanted from the precipitate. Acetonitrile (100 mL) is added to the flask and the mixture is stirred for an additional 30 minutes. The mixture is filtered and the solids are washed with acetonitrile. The acetonitrile is removed from the filtrate by distillation on a rotary evaporator to yield the product as a deep red, viscous liquid that contains 18.9 wt. % Mo and 25.4 wt. % S.

Example 1.5 Preparation of Exemplary Compounds

Preparation of $(nOct_4N)_2[Mo_2S_8O_2]$ 2.47 g of ammonium heptamolybdate tetrahydrate is dissolved in 100 mL of water in a round bottom flask with a magnetic stirrer. Then, 3.72 g of sulfur is dissolved in 17.70 g of a 20% aqueous solution of ammonium sulfide and slowly added to the reaction. The reaction is stirred for 18 hours. A solution of 6.73 g of tetra-n-octylammonium bromide in 100 mL of a solution of methanol:isopropanol (1:1) is prepared and added dropwise to the reaction mixture via an addition funnel. The reaction is stirred for an additional 1 hr at room temperature. The upper aqueous layer is decanted from the precipitate. Acetonitrile (100 mL) is added to the flask and the mixture is stirred for an additional 30 minutes. The mixture is filtered and the solids are washed with acetonitrile. The acetonitrile is removed from the filtrate by distillation on a rotary evaporator to yield the product as a deep red, viscous liquid that contains 12.2 wt. % Mo and 17.4 wt. % S.

Example 1.6 Preparation of Exemplary Compounds

Preparation of $(CetylMe_3N)_2[Mo_2S_8O_2]$ 7.42 g of ammonium heptamolybdate tetrahydrate is dissolved in 300 mL of water in a 3-neck flask with a mechanical stirrer. Then, 11.16 g of sulfur is dissolved in 52.81 g of a 20% aqueous solution of ammonium sulfide and slowly added to the reaction. The reaction is stirred for 16 hrs. A solution of 15.31 g of cetyltrimethylammonium bromide in 175 mL of water is prepared and added dropwise to the reaction mixture via an addition funnel. The addition funnel is rinsed with 50 mL of water and the reaction is stirred for an additional 2 hours at room temperature. The precipitate is filtered and the solids are washed with water until the filtrate is colorless. The solids are suspended in 300 mL of acetonitrile and stirred for an additional 30 minutes. The mixture is filtered and the solids are washed with acetonitrile. The acetonitrile is removed from the filtrate by distillation on a rotary evaporator to yield the product as an orange powder that contains 17.5 wt. % Mo and 25.3 wt. % S.

Example 1.7 Preparation of Exemplary Compounds

Preparation of $(DitallowMe_2N)_2[Mo_2S_8O_2]$ 7.42 g of ammonium heptamolybdate tetrahydrate is dissolved in 300 mL of water in a 3-neck flask with a mechanical stirrer. Then, 11.16 g of sulfur is dissolved in 52.81 g of a 20% aqueous solution of ammonium sulfide and slowly added to the reaction. The reaction is stirred for 16 hours. A solution of 30.79 g of Arquad® 2HT-75 (di(dehydrogenated tallowalkyl)dimethylammonium chloride salt from Akzo Nobel) in 250 mL of a solution of methanol:isopropanol (1:1) is prepared and added to the reaction mixture. The reaction is stirred for an additional 2 hours at room temperature. The precipitate is filtered and the solids are washed with water until the filtrate is colorless. The solids are suspended in 300 mL of acetonitrile and stirred for an additional 30 minutes. The mixture is filtered and the solids are washed with acetonitrile. The acetonitrile is removed from the filtrate by distillation on a rotary evaporator to yield the product as an orange powder that contains 9.6 wt. % Mo and 17.3 wt. % S.

Example 1.8 Preparation of Exemplary Compounds

Preparation of $(MenOct_3N)_2[Mo_2S_8O_2]$ 7.42 g of ammonium heptamolybdate tetrahydrate is dissolved in 300 mL of water in a 3-neck flask with a mechanical stirrer. Then, 11.16 g of sulfur is dissolved in 52.81 g of a 20% aqueous solution of ammonium sulfide and slowly added to the reaction. The reaction is stirred for 20 hours. A solution of 18.84 g of methyltri-n-octylammonium bromide in 150 mL of a solution of methanol:isopropanol (1:1) is prepared and added slowly to the reaction mixture. The reaction is stirred for an additional 30 minutes at room temperature. The upper aqueous layer is decanted from the precipitate. Acetonitrile (300 mL) is added to the flask and the mixture is stirred for an additional 30 minutes. The mixture is filtered and the solids are washed with acetonitrile. The acetonitrile is removed from the filtrate by distillation on a rotary evaporator to yield the product as a deep red-orange, viscous liquid that contains 13.2 wt. % Mo and 22.1 wt. % S.

Example 2: Performance of Additives

Friction and Extreme Pressure Test Methods in Grease

SRV testing was performed according to the ASTM D5707 method (a ball on disc with a 1.00 mm stroke, 200 N, 50 Hz, at 80° C. for 1 hr). The average coefficient of friction and wear volume were determined for each grease formulation. The base grease used was a lithium complex grease manufactured by Citgo and additives were blended into the grease on a hot plate with magnetic stirring for 30 min at 60° C.

4-Ball wear testing was performed according to the ASTM D2266 method (40 kgf, 1200 rpm, 75° C., 1 hr). In this test, one steel ball is rotated on three fixed, evenly spaced steel balls covered in a grease formulation. The average wear scar diameter for the three fixed steel balls was determined for each formulation. The base grease used was a lithium complex grease manufactured by Citgo and additives were blended into the grease on a hot plate with magnetic stirring for 30 min at 60° C.

4-Ball weld testing was performed according to the ASTM D2596 method (1800 rpm, 54° C.). In this test, one steel ball is rotated on three fixed, evenly spaced steel balls covered in a grease formulation at increasing loads for 10 s intervals until welding occurs. The weld point, the load at which the welding occurred, was determined for each grease formulation. The base grease used was a lithium complex grease manufactured by Citgo and additives were blended into the grease on a hot plate with magnetic stirring for 30 min at 60° C.

Frictional and Extreme Pressure Performance of Additives

Data for the performance of additives described herein are provided in Tables 2-7, where a "B" indicates a baseline grease formulation, a "C" indicates a comparison prior art formulation, and an "I" represents the inventive formulations. For these studies, all molybdenum-containing additives were added to lithium complex grease at the treat rates indicated. The treat rates for the other non-molybdenum-containing additives used in combination with molybdenum were either 0.50 or 1.0 wt. %.

In Table 2, a lithium complex grease was treated with MOLYVAN® A and four different quaternary ammonium thiomolybdate salts. The data indicate that all four salts provided lower coefficients of friction as well as reduced wear volumes when compared to the base grease containing no additive. In addition, when the quaternary ammonium oxothiomolybdate salts were compared to the molybdenum dithiocarbamate (MOLYVAN® A is a molybdenum dibutyldithiocarbamate commercially available from Vanderbilt Chemicals, LLC), equivalent or lower coefficients of friction were obtained. Furthermore, all four greases treated with the quaternary ammonium binuclear oxothiomolybdate salts were superior to MOLYVAN® A in terms of reduction in the wear volume. In particular, $(Et_4N)_2[Mo_2S_8O_2]$ had both a lower average coefficient of friction when compared to MOLYVAN® A and nearly a 70% reduction in the wear volume (Table 2, Sample 41). Note that MOLYVAN® A is a well-known antiwear and extreme pressure additive used extensively in grease and lubricant applications (Molybdenum content 27.0-29.0%, Sulfur content 23.5-25.5%). Uses of MOLYVAN® A are discussed in, e.g., U.S. Pat. Nos. 5,612,298, 5,952,273, 6,432,888, and PCT International Application NO. PCT/EP 1997/005914.

For the data included in Table 3, lithium complex grease was treated with MOLYVAN® A and two different quaternary ammonium thiomolybdate salts at lower, intermediate, and higher treat rates with respect to molybdenum. For these studies, the quaternary ammonium thiomolybdate salts examined were $(Me_4N)_2[Mo_2S_8O_2]$ and $(Et_4N)_2[Mo_2S_8O_2]$. The data indicate that all the molybdenum-containing greases reduced the wear volume at each treat rate compared to the base grease containing no additives. In addition, when the greases containing $(Et_4N)_2[Mo_2S_8O_2]$ were compared to MOLYVAN® A at each treat rate, equivalent or lower average coefficients of friction were observed. Furthermore, the wear volumes at each treat rate for $(Et_4N)_2[Mo_2S_8O_2]$ were significantly lower compared to MOLYVAN® A with reductions of 25% (Table 3, 8C and 14I), 70% (Table 3, 9C and 15I), and 86% (Table 3, 10C and 16I). The combination of two different classes of molybdenum-based additives was also investigated with each additive contributing 4200 ppm of molybdenum to the lubricant composition. Interestingly, while the combination of $(Et_4N)_2[Mo_2S_8O_2]$ and MOLYVAN® A led to a slight decrease in the average coefficient of friction, a dramatic increase in the wear volume was observed (Table 3, 18I). Surprisingly, the 1:1 with respect to molybdenum combination of $(Me_4N)_2[Mo_2S_8O_2]$ and MOLYVAN® A led to both a small decrease in the average coefficient of friction and an unexpectedly large reduction in the wear volume. When compared to each additive alone at 8400 ppm of molybdenum (Table 3, 9C and 12I), the combination of the two additives at 4200 ppm molybdenum each resulted in approximately a 50% reduction in the wear volume (Table 3, 17I).

Tables 4-6 describe performance results from the combination of molybdenum-containing additives with other classes of lubricant additives. The data presented in Table 4 are for the combination of molybdenum additives with VANLUBE® 7611 M, an ashless phosphorodithiolate additive used as an antiwear agent. When the quaternary ammonium binuclear oxothiomolybdate salts and VANLUBE® 7611 M were compared to MOLYVAN® A, all three salts in combination with VANLUBE® 7611 M provided equivalent reductions in friction while also reducing the wear volume significantly. Both $(CetylMe_3N)_2[Mo_2S_8O_2]$ and $(DitallowMe_2N)_2[Mo_2S_8O_2]$ with VANLUBE® 7611 M resulted in approximately 25% reductions in the wear volume (Table 4, Samples 22I and 23I) while $(Et_4N)_2[Mo_2S_8O_2]$ reduced the wear volume by over 80% (Table 4, Sample 21I). For the data presented in Table 5, lithium complex grease was treated with molybdenum-containing additives and VANLUBE® AZ, a zinc dithiocarbamate used as an antiwear agent, at two treat rates. The data indicated that all four quaternary ammonium binuclear oxothiomolybdate salts when combined with VANLUBE® AZ provided lower coefficients of friction as well as reduced wear volumes when compared to the base grease containing no additives. Furthermore, both $(Me_4N)_2[Mo_2S_8O_2]$ and $(Et_4N)_2 [Mo_2S_8O_2]$ with VANLUBE® AZ provided superior reduction in the wear volume (55 and 85% lower respectively) when compared to MOLYVAN® A using 0.50% VANLUBE® AZ (Table 5, Samples 25C, 27I, and 29I). The reductions in wear volume of $(Me_4N)_2[Mo_2S_8O_2]$ and $(Et_4N)_2[Mo_2S_8O_2]$ compared to MOLYVAN® A when using 1.00% VANLUBE® AZ marginally improved to 60 and 87% respectively (Table 5, Samples 26C, 28I, and 30I). The data for lithium complex grease treated with the combination of molybdenum-containing additives and OLOA® 262, a zinc dialkyldithiophosphate used as an antiwear agent available from ChevronOronite Company LLC, are included in Table 6 at two treat rates of OLOA® 262. For this series, the quaternary ammonium oxothiomolybdate salts with OLOA® 262 provided lower coefficients of friction as well as reduced wear volumes when compared to the base grease without any additives. Furthermore, the wear volumes of the combination of either $(Me_4N)_2[Mo_2S_8O_2]$ and $(Et_4N)_2 [Mo_2S_8O_2]$ with OLOA® 262 at 0.50% (Table 6, Samples 36I and 38I) were approximately 40% lower than that of the combination containing MOLYVAN® A (Table 6, Sample 34C). Notably when 1.00% OLOA® 262 was used, the grease containing $(Me_4N)_2[Mo_2S_8O_2]$ had both a lower average coefficient of friction and a 42% reduction in the wear volume when compared to the combination containing MOLYVAN® A (Table 6, Samples 35C and 37I).

Finally, the performance of $(Me_4N)_2[Mo_2S_8O_2]$ and $(Et_4N)_2[Mo_2S_8O_2]$ as an extreme pressure additives were evaluated and compared to that of Vanderbilt Chemicals, LLC products MOLYVAN® A, VANLUBE® 829 (5,5-dithiobis-(1,3,4-thiadiazole-2(3H)-thione, an antiwear agent, antioxidant, and extreme pressure additive) and VANLUBE® 972 M (a thiadiazole derivative in polyalkylene glycol, an ashless extreme pressure additive and corrosion inhibitor) (Table 7). The data indicate that the performance of $(Et_4N)_2[Mo_2S_8O_2]$ was superior to that of MOLYVAN® A and comparable to VANLUBE® 972M. Although the extreme pressure performance of $(Et_4N)_2[Mo_2S_8O_2]$ was comparable to VANLUBE® 972 M and inferior to VANLUBE® 829, the quaternary ammonium binuclear oxothiomolybdate salt also exhibited a marked reduction in the wear volume when compared to the other two additives. These data indicated that $(Et_4N)_2[Mo_2S_8O_2]$ can provide extreme pressure performance with an additional benefit in terms of wear reduction. Interestingly, the 4-ball weld point for $(Me_4N)_2[Mo_2S_8O_2]$ (Table 7, Sample 44C) was higher than MOLYVAN® A, $(ELN)_2[Mo_2S_8O_2]$, and VANLUBE® 972 M while still reducing the 4-ball wear compared to the base grease containing no additives.

TABLE 2

| Sample | 1B | 2C | 3I | 4I | 5I | 6I |
|---|---|---|---|---|---|---|
| MOLYVAN ® A | | 3.00 | | | | |
| $(Me_4N)_2[Mo_2S_8O_2]$ | | | 2.74 | | | |
| $(Et_4N)_2[Mo_2S_8O_2]$ | | | | 3.62 | | |
| $(CetylMe_3N)_2[Mo_2S_8O_2]$ | | | | | 4.80 | |
| $(DitallowMe_2N)_2[Mo_2S_8O_2]$ | | | | | | 8.75 |
| Axel Li-Complex | 100.00 | 97.00 | 97.26 | 96.38 | 95.20 | 91.25 |
| Total Molybdenum (ppm) | 0 | 8400 | 8400 | 8400 | 8400 | 8400 |
| ASTM D5707 | | | | | | |
| Final Friction, μ | | 0.176 | 0.124 | 0.126 | 0.126 | 0.108 | 0.08 |
| Average Friction, μ | | 0.173 | 0.117 | 0.112 | 0.104 | 0.069 | 0.088 |
| Wear Volume, μm³ | 4,500,938 | 296,928 | 188,879 | 94,266 | 38,486 | 275,729 |

TABLE 3

| Sample | 7B | 8C | 9C | 10C | 11I | 12I |
|---|---|---|---|---|---|---|
| MOLYVAN ® A | | 1.00 | 3.00 | 5.00 | | |
| $(Me_4N)_2[Mo_2S_8O_2]$ | | | | | 0.92 | 2.74 |
| $(Et_4N)_2[Mo_2S_8O_2]$ | | | | | | |
| Axel Li-Complex | 100.00 | 99.00 | 97.00 | 95.00 | 99.08 | 97.26 |
| Total Molybdenum (ppm) ASTM D5707 | 0 | 2800 | 8400 | 14000 | 2800 | 8400 |
| Final Friction, μ | 0.133 | 0.147 | 0.135 | 0.123 | 0.150 | 0.126 |
| Average Friction, μ | 0.131 | 0.134 | 0.116 | 0.098 | 0.140 | 0.112 |
| Wear Volume, μm3 | 1,113,164 | 500,062 | 173,914 | 253,956 | 527,755 | 188,879 |

| Sample | 13I | 14I | 15I | 16I | 17I | 18I |
|---|---|---|---|---|---|---|
| MOLYVAN ® A | | | | | 1.50 | 1.50 |
| $(Me_4N)_2[Mo_2S_8O_2]$ | 4.58 | | | | 1.37 | |
| $(Et_4N)_2[Mo_2S_8O_2]$ | | 1.13 | 3.39 | 5.64 | | 1.70 |
| Axel Li-Complex | 95.42 | 98.87 | 96.61 | 94.36 | 97.13 | 96.81 |
| Total Molybdenum (ppm) ASTM D5707 | 14000 | 2800 | 8400 | 14000 | 8400 | 8400 |
| Final Friction, μ | 0.129 | 0.133 | 0.199 | 0.104 | 0.126 | 0.119 |
| Average Friction, μ | 0.111 | 0.131 | 0.105 | 0.102 | 0.107 | 0.100 |
| Wear Volume, μm3 | 90,239 | 375,438 | 51,953 | 34,191 | 93,928 | 488,882 |

TABLE 4

| | Sample | | | | |
|---|---|---|---|---|---|
| | 19B | 20C | 21I | 22I | 23I |
| VANLUBE ® 7611 M | | 0.50 | 0.50 | 0.50 | 0.50 |
| MOLYVAN ® A | | 3.00 | | | |
| $(Et_4N)_2[Mo_2S_8O_2]$ | | | 3.62 | | |
| $(CetylMe_3N)_2[Mo_2S_8O_2]$ | | | | 4.80 | |
| $(DitallowMe_2N)_2[Mo_2S_8O_2]$ | | | | | 8.75 |
| Axel Li-Complex | 100.00 | 96.50 | 95.88 | 94.70 | 90.75 |
| Total Molybdenum (ppm) ASTM D5707 | 0 | 8400 | 8400 | 8400 | 8400 |
| Final Friction, μ | 0.176 | 0.101 | 0.116 | 0.122 | 0.102 |
| Average Friction, μ | 0.173 | 0.93 | 0.113 | 0.123 | 0.089 |
| Wear Volume, μm³ | 4,500,938 | 280,723 | 51,748 | 219,092 | 201,103 |

TABLE 5

| Sample | 24B | 25C | 26C | 27I | 28I |
|---|---|---|---|---|---|
| VANLUBE ® AZ | | 0.50 | 1.00 | 0.50 | 1.00 |
| MOLYVAN ® A | | 3.00 | 3.00 | | |
| $(Me_4N)_2[Mo_2S_8O_2]$ | | | | | |
| $(Et_4N)_2[Mo_2S_8O_2]$ | | | | 2.74 | 2.74 |
| $(CetylMe_3N)_2[Mo_2S_8O_2]$ | | | | | |
| $(DitallowMe_2N)_2[Mo_2S_8O_2]$ | | | | | |
| Axel Li-Complex | 100.00 | 96.50 | 96.00 | 96.76 | 96.26 |
| Total Molybdenum (ppm) ASTM D5707 | 0 | 8400 | 8400 | 8400 | 8400 |
| Final Friction, μ | 0.133 | 0.119 | 0.084 | 0.097 | 0.096 |
| Average Friction, μ | 0.131 | 0.105 | 0.08 | 0.092 | 0.078 |
| Wear Volume, μm3 | 1,113,164 | 124,514 | 87,823 | 56,565 | 35,169 |

| Sample | 29I | 30I | 31I | 32I |
|---|---|---|---|---|
| VANLUBE ® AZ | 0.50 | 1.00 | 0.50 | 0.50 |
| MOLYVAN ® A | | | | |
| $(Me_4N)_2[Mo_2S_8O_2]$ | | | | |
| $(Et_4N)_2[Mo_2S_8O_2]$ | 3.39 | 3.39 | | |
| $(CetylMe_3N)_2[Mo_2S_8O_2]$ | | | 4.80 | |
| $(DitallowMe_2N)_2[Mo_2S_8O_2]$ | | | | 8.75 |
| Axel Li-Complex | 96.11 | 95.61 | 94.70 | 90.75 |
| Total Molybdenum (ppm) | 8400 | 8400 | 8400 | 8400 |

TABLE 5-continued

| ASTM D5707 | | | | |
|---|---|---|---|---|
| Final Friction, μ | 0.073 | 0.076 | 0.139 | 0.104 |
| Average Friction, μ | 0.081 | 0.085 | 0.119 | 0.087 |
| Wear Volume, μm3 | 19,693 | 11,870 | 331,926 | 190,451 |

TABLE 6

| Sample | 33B | 34C | 35C | 36I | 37I |
|---|---|---|---|---|---|
| OLOA ® 262 | | 0.50 | 1.00 | 0.50 | 1.00 |
| MOLYVAN ® A | | 3.00 | 3.00 | | |
| $(Me_4N)_2[Mo_2S_8O_2]$ | | | | 2.74 | 2.74 |
| $(Et_4N)_2[Mo_2S_8O_2]$ | | | | | |
| $(CetylMe_3N)_2[Mo_2S_8O_2]$ | | | | | |
| $(DitallowMe_2N)_2[Mo_2S_8O_2]$ | | | | | |
| Axel Li-Complex | 100.00 | 96.50 | 96.00 | 96.76 | 96.26 |
| Total Molybdenum (ppm) | 0 | 8400 | 8400 | 8400 | 8400 |
| ASTM D5707 | | | | | |
| Final Friction, μ | 0.133 | 0.069 | 0.055 | 0.087 | 0.061 |
| Average Friction, μ | 0.131 | 0.082 | 0.064 | 0.088 | 0.062 |
| Wear Volume, μm3 | 1,113,164 | 84,679 | 23,121 | 53,882 | 13,454 |

| Sample | 38I | 39I | 40I | 41I |
|---|---|---|---|---|
| OLOA ® 262 | 0.50 | 1.00 | 0.50 | 0.50 |
| MOLYVAN ® A | | | | |
| $(Me_4N)_2[Mo_2S_8O_2]$ | | | | |
| $(Et_4N)_2[Mo_2S_8O_2]$ | 3.39 | 3.39 | | |
| $(CetylMe_3N)_2[Mo_2S_8O_2]$ | | | 4.80 | |
| $(DitallowMe_2N)_2[Mo_2S_8O_2]$ | | | | 8.75 |
| Axel Li-Complex | 96.11 | 95.61 | 94.70 | 90.75 |
| Total Molybdenum (ppm) | 8400 | 8400 | 8400 | 8400 |
| ASTM D5707 | | | | |
| Final Friction, μ | 0.098 | 0.059 | 0.125 | 0.117 |
| Average Friction, μ | 0.085 | 0.08 | 0.110 | 0.090 |
| Wear Volume, μm3 | 45,482 | 21,363 | 68,346 | 153,640 |

TABLE 7

| Sample | 42B | 43C | 44C | 45C | 46I | 47I |
|---|---|---|---|---|---|---|
| MOLYVAN ® A | | 3.01 | | | | |
| VANLUBE ® 829 | | | 3.37 | | | |
| VANLUBE ® 972 M | | | | 3.37 | | |
| $(Me_4N)_2[Mo_2S_8O_2]$ | | | | | 2.74 | |
| $(Et_4N)_2[Mo_2S_8O_2]$ | | | | | | 3.37 |
| Axel Li-Complex | 100.00 | 96.99 | 96.63 | 96.63 | 97.26 | 96.63 |
| Total Molybdenum (ppm) | 0 | 8400 | 0 | 0 | 8400 | 8400 |
| ASTM D2596 | | | | | | |
| 4-Ball Weld, kgf | 200 | 250 | 800+ | 500 | 620 | 500 |
| ASTM D2266 | | | | | | |
| Wear scar, mm | 0.80 | 0.40 | 0.56 | 0.60 | 0.62 | 0.40 |

What is claimed is:

1. A compound of Formula I:

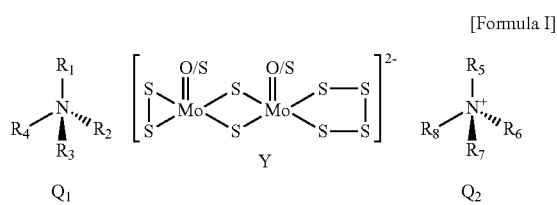

[Formula I]

wherein
$R_1$-$R_4$ and $R_5$-$R_8$ are independently selected from the group consisting of hydrocarbyl groups and hydrocarbyl groups containing heteroatoms, such that the total carbon atoms from counterions $Q_1$ and $Q_2$ is from 10 to 76, wherein $Q_1$ and $Q_2$ are not tetramethylammonium or tetraethylammonium; and
molybdate anion (Y) is a binuclear sulfur-containing dianion selected from the group consisting of $[Mo_2S_8O_2]^{2-}$, $[Mo_2S_9O]^{2-}$, and $[Mo_2S_{10}]^{2-}$, and mixtures thereof.

2. The compound of claim 1, wherein the hydrocarbyl groups are straight-chain, branched, or cyclic hydrocarbons and saturated or unsaturated hydrocarbons from 1 to 18 carbon atoms each.

3. The compound of claim 2, wherein the hydrocarbyl groups have from 1 to 4 carbon atoms each.

4. The compound of claim 1, wherein $Q_1$ and $Q_2$ are the same.

5. The compound of claim 1, herein $Q_1$ and $Q_2$ are independently selected from the group consisting of alkyltrimethylammonium, dialkyldimethylammonium, trialkylmethylammonium, alkyltriethylammonium, dialkyldiethylammonium, and trialkylethylammonium.

6. The compound of claim 5, wherein the $Q_1$ and $Q_2$ are independently selected from the group consisting of tetrabutylammonium, tetraoctylammonium, tetradecylammonium, methyltrioctylammonium, cetyltrimethylammonium and dimethylditallowammonium.

7. The compound of claim 6, wherein $Q_1=Q_2$ and wherein $Y=[Mo_2S_8O_2]^{2-}$.

8. The compound of claim 1, wherein the combination of Q1 and Q2 with Y is a compound that is liquid under 100° C.

9. The compound of claim 8, wherein the compound is butanaminium, NNN-tributyl-, stereoisomer of (dithio)dioxo(tetrathio)di-μ-thioxodimolybdate(2-) (Mo—Mo) (2:1).

10. A lubricating composition comprising a lubricant base oil or grease, and a compound of Formula I:

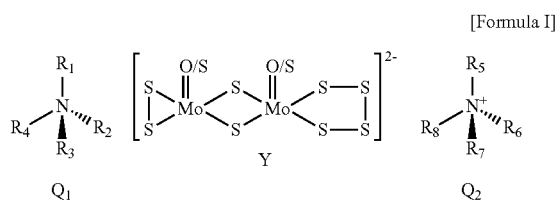

[Formula I]

wherein
$R_1$-$R_4$ and $R_5$-$R_8$ are independently selected from the group consisting of hydrocarbyl groups, such that the total carbon atoms from counterions $Q_1$ and $Q_2$ is from 8 to 76, and
molybdate anion (Y) is a binuclear sulfur-containing dianion selected from the group consisting of $[Mo_2S_8O_2]^{2-}$, $[Mo_2S_9O]^{2-}$, and $[Mo_2S_{10}]^{2-}$, and mixtures thereof,
wherein the compound of Formula I is present in an amount sufficient to provide about 100-15,000 ppm molybdenum to the lubricating composition.

11. The lubricating composition of claim 10, wherein the hydrocarbyl groups are straight-chain, branched, or cyclic hydrocarbons and saturated or unsaturated hydrocarbons from 1 to 18 carbon atoms each.

12. The lubricating composition of claim 11, wherein the hydrocarbyl groups have from 1 to 4 carbon atoms each.

13. The lubricating composition of claim 10, wherein $Q_1$ and $Q_2$ are the same.

14. The lubricating composition of claim 10, wherein $R_4$ and $R_8$ taken together are a mono- or polyalkylene oxide such that $Q_1$ and $Q_2$ are linked.

15. The lubricating composition of claim 10, wherein $Q_1$ and $Q_2$ are independently selected from the group consisting of alkyltrimethylammonium, dialkyldimethylammonium, trialkylmethylammonium, alkyltriethylammonium, dialkyldiethylammonium, and trialkylethylammonium.

16. The lubricating composition of claim 10, wherein the $Q_1$ and $Q_2$ are independently selected from the group consisting of tetramethylammonium, tetraethylammonium, tetrabutylammonium, tetraoctylammonium, tetradecylammonium, methyltrioctylammonium, cetyltrimethylammonium and dimethylditallowammonium.

17. The lubricating composition of claim 16, wherein $Q_1=Q_2$, and $Y=[Mo_2S_8O_2]^{2-}$.

18. The lubricating composition of claim 10, wherein the compound of Formula I is at an amount sufficient to deliver about 2800-14,000 ppm of molybdenum to the lubricating composition.

19. The lubricating composition of claim 10, further comprising a molybdenum dialkyldithiocarbamate at an amount such that the combination of molybdenum dialkyldithiocarbamate and compound of Formula I combine to deliver a total of 100-15,000 ppm of molybdenum to the lubricating composition.

20. The lubricating composition of claim 19, wherein the molybdenum dialkyldithiocarbamate is molybdenum dibutyldithiocarbamate.

21. The lubricating composition of claim 10, further comprising a phosphorous or zinc-containing anti-wear compound at 0.005 wt. % to 10.000 wt. %.

22. The lubricating composition of claim 21, wherein the phosphorus or zinc containing anti-wear compound is selected from the group consisting of zinc dialkyldithiocarbamates, zinc dialkyldithiophosphates, dialkyldithiophosphoric acid esters, and amine salts of alkyl acid phosphates.

23. The lubricating composition of claim 10, wherein the lubricant base is a grease.

24. The lubricating composition of claim 23, wherein the grease is a lithium complex grease.

25. The lubricating composition of claim 10, wherein the lubricant base is a lithium complex grease; $Q_1=Q_2$, and are chosen from the group consisting of tetramethylammonium ($Me_4N$), tetraethylammonium ($Et_4N$), tetra-n-butylammonium ($nBu_4N$), tetra-n-octylammonium ($nOct_4N$), methyl-tri-n-octylammonium ($MenOct_3N$), hexadecyltrimethylammonium ($CetylMe_3N$), and di(hydrogenated tallowalkyl)dimethylammonium ($DitallowMe_2N$); $Y=[Mo_2S_8O_2]^{2-}$; and the compound of Formula I is at an amount sufficient to deliver about 2800-14,000 ppm of molybdenum to the lubricating composition.

* * * * *